(12) United States Patent
Flinsenberg et al.

(10) Patent No.: US 8,749,391 B2
(45) Date of Patent: Jun. 10, 2014

(54) FALL DETECTION SYSTEM

(75) Inventors: Ingrid Christina Maria Flinsenberg, Eindhoven (NL); Warner Rudoph Theophile Ten Kate, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 278 days.

(21) Appl. No.: 13/124,205

(22) PCT Filed: Oct. 7, 2009

(86) PCT No.: PCT/IB2009/054391
§ 371 (c)(1),
(2), (4) Date: Apr. 14, 2011

(87) PCT Pub. No.: WO2010/044013
PCT Pub. Date: Apr. 22, 2010

(65) Prior Publication Data
US 2011/0199216 A1    Aug. 18, 2011

(30) Foreign Application Priority Data
Oct. 16, 2008   (EP) .................................... 08166745

(51) Int. Cl.
*G08B 23/00*   (2006.01)
*G08B 1/08*    (2006.01)
*G08B 5/00*    (2006.01)
*G08B 21/00*   (2006.01)

(52) U.S. Cl.
USPC .................. 340/573.1; 340/984; 340/539.12; 340/669; 340/540

(58) Field of Classification Search
USPC .................. 340/573.1, 539.12, 669, 540, 984
See application file for complete search history.

(56) References Cited

U.S. PATENT DOCUMENTS

| | | | | |
|---|---|---|---|---|
| 6,208,251 | B1 * | 3/2001 | Cadet et al. | 340/573.1 |
| 6,433,690 | B2 * | 8/2002 | Petelenz et al. | 340/573.1 |
| 7,961,109 | B2 * | 6/2011 | Jang et al. | 340/573.1 |
| 8,206,325 | B1 * | 6/2012 | Najafi et al. | 600/595 |
| 2003/0058111 | A1 * | 3/2003 | Lee et al. | 340/573.1 |

(Continued)

FOREIGN PATENT DOCUMENTS

| | | |
|---|---|---|
| EP | 1870037 | 12/2007 |
| GB | 2323196 | 9/1998 |
| WO | 2005016143 | 2/2005 |
| WO | 2007081629 | 7/2007 |

OTHER PUBLICATIONS

Podsiadlo et al: "The Timed "Up & Go": A Test of Basic Functional Mobility for Frail Elderly Persons."; J. Am. Geriatric Society, vol. 39, February 1991, pp. 142-148.

(Continued)

*Primary Examiner* — George Bugg
*Assistant Examiner* — Munear Akki

(57) ABSTRACT

There is provided a fall detection system, comprising one or more sensors for monitoring the movement of a user of the fall detection system and for generating corresponding signals; means for determining a threshold from one or more measurements of the physical condition of the user; a processor for analyzing the signals to identify a fall by the user; analyzing the signals to identify a period of inactivity of the user following the fall; and comparing the length of the period of inactivity of the user with the threshold to determine the severity of the fall.

20 Claims, 2 Drawing Sheets

(56) References Cited

U.S. PATENT DOCUMENTS

2006/0139166 A1    6/2006   Choutier et al.
2006/0214806 A1*   9/2006   Clifford et al. ............ 340/573.1
2006/0279426 A1   12/2006   Bonnet et al.
2008/0129518 A1    6/2008   Carlton-Foss

OTHER PUBLICATIONS

Buatois et al: "Five Times Sit to Stand Test Is a Predictor of Recurrent Falls in Healthy Community-Living Subjects Aged 65 and Older"; J. Am. Geriatric Society, vol. 56, No. 8, Aug. 2008, pp. 1575-1577.

* cited by examiner

FALL DETECTION SYSTEM

TECHNICAL FIELD OF THE INVENTION

The invention relates to a fall detection system and a method of operating a fall detection system, and in particular to a fall detection system and a method of operating a fall detection system that provides an indication of the severity of a fall.

BACKGROUND TO THE INVENTION

Falling is a significant problem in the care of the elderly that can lead to morbidity and mortality. From a physical perspective, falls cause injuries, while from the mental perspective, falls cause fear-of-falling, which in turn leads to social isolation and depression.

Fall detection systems are being developed which can provide an automated and reliable means for detecting when a user has fallen. If a fall is detected, the system issues an alarm which summons help to the user. This assures the user that adequate measures will be taken in the event that a fall occurs.

Commonly, automated fall detection systems are based on an accelerometer that is to be attached to the user's body. The fall detection system tracks the signals from the accelerometer and determines that a fall has taken place if a characteristic pattern is identified. A typical pattern is a combination of a high impact value in which the acceleration signal exceeds a preconfigured threshold, followed by a period of relative or actual inactivity characterised by relatively constant acceleration, for example gravity only (or no acceleration depending on the type of accelerometer used), since the user is lying motionless on the ground. The pattern may continue by revealing activity, deviating from the relatively constant period of acceleration, when the user stands up again.

Some fall detection systems can determine an inability of the user to get up after a fall (as represented by an extended period of inactivity), and use this determination to trigger or issue an alarm signal. One such system is described in WO 2005/016143.

SUMMARY OF THE INVENTION

In the known systems, there is a single fixed time period for measuring the inability of the user to get up after a fall, which means that this time period is the same for each possible user of the fall detection system. Thus, this time period is set at some value, regardless of the physical condition of the user and their personal ability to stand up from the ground. The typical time taken for a user to get up can range from a few seconds (say 2-3) for users that are young and healthy to tens of seconds (say 15-45) for users that are elderly and frail.

Thus, in setting a single time period for the fall detection system, there is a trade off to be made between choosing a conservative value that might result in a user falling, not being able to get up and having to wait for tens of seconds before an alarm is issued or help summoned, and a shorter period that results in an alarm being issued before the user has had a chance to get up on their own (at their own pace).

Therefore, it is an object of the invention to provide a fall detection system and a method of operating a fall detection system that overcomes the disadvantages with the prior art systems described above.

According to a first aspect of the invention, there is provided a fall detection system, comprising one or more sensors for monitoring the movement of a user of the fall detection system and for generating corresponding signals; means for determining a threshold from one or more measurements of the physical condition of the user; a processor for analysing the signals to identify a fall by the user; analysing the signals to identify a period of inactivity of the user following the fall; and comparing the length of the period of inactivity of the user with the threshold to determine the severity of the fall.

Preferably, the processor is adapted to determine that the fall is severe in the event that the length of the period of inactivity of the user exceeds the threshold.

Preferably, the processor is adapted to trigger an alarm and/or summon help to the user if the fall is severe.

In preferred embodiments, the processor is adapted to analyse the signals to identify the end of the period of inactivity when the user gets up.

In some embodiments, the processor is adapted to determine that the fall is not severe in the event that the length of the period of inactivity of the user is less than the threshold.

In alternative embodiments, the processor is adapted to grade the severity of the fall in the event that the length of the period of inactivity of the user is less than the threshold using a ratio of the length of the period of inactivity to the threshold. The processor can then trigger an alarm and/or summon help to the user on the basis of the determined severity grade.

Preferably, the one or more sensors comprises an accelerometer for measuring the acceleration of the fall detection system.

In some embodiments, the processor is adapted to identify a fall by identifying an impact that is characteristic of a fall. The processor can identify an impact by identifying one or more peaks in the measurements of the acceleration. The processor can be further adapted to determine the severity of the fall by determining the magnitude of the acceleration in the impact.

Preferably, the one or more measurements of the physical condition of the user comprise measurements of a predetermined movement or series of movements by the user.

In specific embodiments, the predetermined movement or series of movements comprises one or more of a sit-to-stand transfer, timed up and go movement, getting up from a bed and getting up from the ground.

In some embodiments, the one or more measurements comprise measurements of the time taken for the user to complete the predetermined movement or series of movements.

In a preferred embodiment, the processor comprises the means for determining the threshold; and the processor is adapted to determine the one or more measurements of the physical condition of the user while the fall detection system is in use by the user.

According to a second aspect of the invention, there is provided a method of operating a fall detection system, the method comprising determining a threshold from one or more measurements of the physical condition of a user of the fall detection system; detecting a fall by the user; and monitoring the length of a period of inactivity of the user following the fall relative to the threshold to determine the severity of the fall.

According to a third aspect of the invention, there is provided a computer program product for use in a fall detection system, the computer program product comprising computer program code that, when executed on a processor or computer, is adapted to determine a threshold from one or more measurements of the physical condition of a user of the fall detection system; detect a fall by the user; and monitor the length of a period of inactivity of the user following the fall relative to the first threshold to determine the severity of the fall.

BRIEF DESCRIPTION OF THE DRAWINGS

The invention will now be described, by way of example only, with reference to the following drawings, in which.

DETAILED DESCRIPTION OF THE PREFERRED EMBODIMENTS

Figure 1:
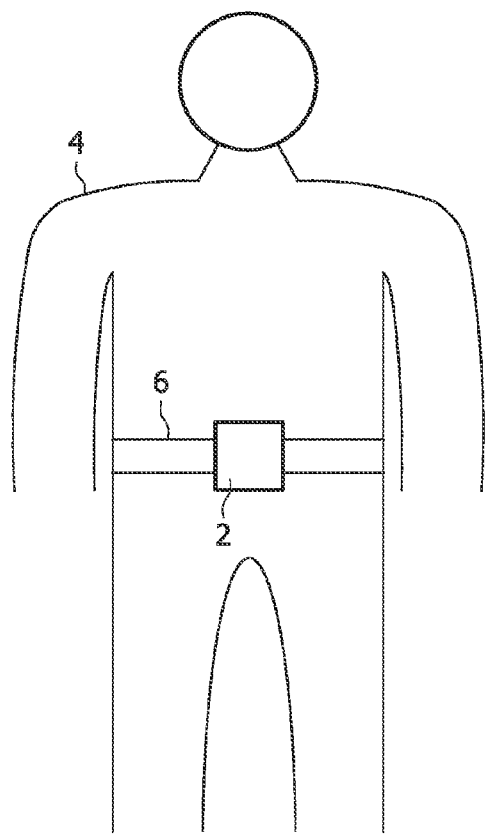
FIG. 1 shows a fall detection system attached to a user.

FIG. 1 shows a fall detection system 2 attached to a user 4 via a band or other attachment means 6. The fall detection system 2 is preferably attached at the upper part of the user's body 4, such as around the waist, at the wrist, or as a pendant around the neck.

If the fall detection system 2 detects a fall by the user 4, an alarm signal can be broadcast (e.g. audibly) from the fall detection system 2 or it can be transmitted (e.g. wirelessly) to a call-centre or other assistance unit, unless the user 4 gets up from the ground quickly.

Figure 2:
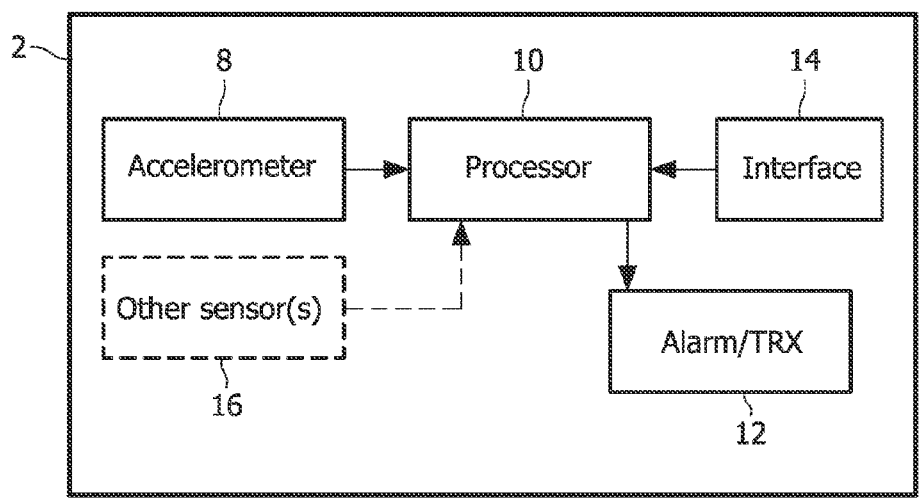
FIG. 2 is a block diagram of the fall detection system.

FIG. 2 is a block diagram of a fall detection system 2 in accordance with the invention.

The system 2 comprises an accelerometer 8 that measures the acceleration experienced by the fall detection system 2 (and hence the user 4 when the fall detection system 2 is attached to their body) and generates signals indicative of the measured acceleration, a processor 10 for processing the signals from the accelerometer 8 to determine if the user 4 has fallen, and an alarm (and/or transmitter/transceiver circuitry) 12 for summoning help in the event that the user 4 has fallen.

The system 2 further comprises an interface 14, which can be in the form of an input/output port for receiving electronic signals from another device, or can comprise one or more buttons or switches with proper user-feedback indication that allow a user 4 or care provider to interact with the fall detection system 2. The purpose of the interface 14 will be described further below.

In some embodiments, the fall detection system 2 can further comprise one or more other sensors 16 that detect characteristics of movement of the user 4 (other than acceleration) and that generate corresponding signals. These signals can then be used by the processor 10 in combination with the signals from the accelerometer 8 to determine if the user has fallen. The one or more sensors 16 can comprise a magnetometer, gyroscope, altimeter and/or any other suitable sensor.

As described above, the processor 10 monitors the signals from the accelerometer 8 to determine if a fall has taken place. Falls are often characterised by a large impact (when the user 4 hits the ground) represented by a relatively large and sudden (i.e. short in duration) acceleration in the vertical direction, followed by a period of little or no activity while the user 4 lays on the ground, represented by a period of relatively constant acceleration (this constant acceleration will usually be zero or gravity, depending on the type of accelerometer used). The processor 10 monitors the length of the period of inactivity, and determines that the fall is severe if the length of the period exceeds a threshold, and an alarm is issued.

It will also be appreciated that certain types of falls may have less clear impacts, and the algorithm used in the processor 10 can recognise these as well by relaxing the requirement for a large but short acceleration characteristic.

Figure 3:
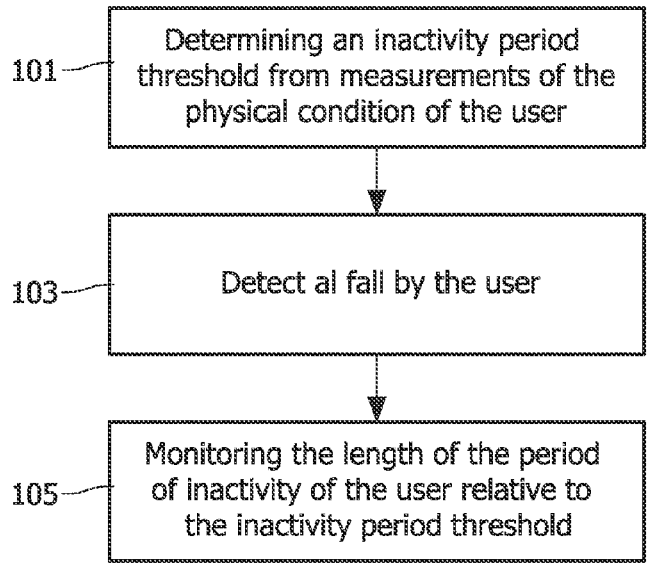
FIG. 3 is a flow chart illustrating a method in accordance with the invention.

A flow chart illustrating a method in accordance with the invention is shown in FIG. 3. In contrast to the prior art systems where there is a single threshold value for all users 4, the invention provides that the threshold is determined from measurements of the physical condition of the user 4 (step 101). Once a fall has been detected (step 103), the threshold is compared to the period of inactivity following the fall to determine if the fall was severe (step 105).

In one embodiment, the threshold can be manually set prior to the first use of the fall detection system 2 by the user 4, and re-evaluated at regular intervals (of the order of days, weeks or months) to make sure that the threshold is adapted to the physical condition of the user 4 over time.

As an alternative to setting the threshold manually, a preferred embodiment provides that the fall detection system 2 itself is used to measure the time it takes the user 4 to perform certain representative movements or activities, such as a Sit-To-Stand (STS) transfer, or getting out of bed, during use of the fall detection system 2. For example, the fall detection system 2 can evaluate the signals from the accelerometer 8 and other sensors 16 (if present) to detect when the representative movements or activities are taking place.

These movements are carried out regularly during the course of a normal day and the time taken to perform these movements can be used to estimate the time (and thus the inactivity period threshold) it would take the user 4 to stand up after a fall. In particular, the fall detection system 2 can determine whether a fall is severe if the user 4 is unable to stand up again within a multiple of this time period. If the user 4 did not stand up, the fall can be considered to be severe.

The system 2 can also account for the time that the user 4 may be confused by the fall, which extends the time that they will lie on the ground. In the first order, this time is proportional to the time taken for the observed activities, although other measures can be used.

In further preferred embodiments, if the user 4 does stand up after a fall, the severity of the fall can be graded by evaluating the ratio of the estimated time needed to stand up again (i.e. the inactivity period threshold) and the measured time taken to stand up.

This ratio, or the measured time taken to stand up, can also be used to refine the inactivity period threshold, as described further below.

The threshold can be set (effectively manually) by evaluating the results of certain movement tests that indicate the physical condition of the user 4, such as the mentioned STS transfer (Buatois et al., J. Am. Geriatr. Soc. 56 (2008) 1575-1577), the Timed Up and Go (TUG) test (Podsiadlo et al, J. Am. Geriatr. Soc. 39 (1991) 142-148), or any other standard fall risk tests, such as the time to stand up from a chair or bed, or a combination of several tests.

The TUG test is a standard method to determine whether a user 4 is at risk of falling by measuring the time it takes the user 4 to stand up from a chair, walk three meters, turn around, walk back to the chair and sit down. If this exercise takes the user 4 more than 30 seconds, say, they can be considered to have a high risk of falling. If it takes less than 20 seconds, say, the user 4 can be considered to have a low risk of falling. The interval between 20 and 30 seconds is considered to be a transition phase. The inactivity period threshold can be set based on the result of the TUG test. In the case of a TUG result of less than 20 seconds, the threshold can be set to a relatively low value, of the order of 5-8 seconds, while for a TUG result of more than 30 seconds, the threshold can be set to a relatively high value, of the order of 15-20 seconds. For TUG results between 20 and 30 seconds, either of the high or low values can be used for the threshold, but it is also possible for the threshold to increase linearly from the low value to the high value.

An alternative test is to measure the time it takes the user 4 to stand up from a chair, which is referred to as the Sit-To-Stand (STS) transfer duration. The threshold can be set to the STS duration plus 3 seconds, for example. Alternatively, it is possible to measure the time it takes the user 4 to stand up after lying on a bed. The threshold can be set to the measured time plus 1 second, for example. Alternatively, it is possible to measure the time it takes the user 4 to stand up after lying on the floor. The threshold can be set to the measured time, for example. By carrying out more than one test, the threshold can be determined more reliably by taking the maximum of the resulting time periods from each of the tests, or by taking a weighted average of the time periods.

The determined threshold can be provided to the processor 10 of the fall detection system 2 using the interface 14. Alternatively, the results of the tests (whether of the individual tests or a combined result) can be provided to the processor 10, and the processor 10 can determine the threshold from the results (perhaps using a look-up table or similar). In particular, if the interface 14 is an input/output port, the threshold or results of the tests can be provided from another electronic device, whereas if the interface 14 is a keypad or similar, the results of the tests can be manually input by the user 4 or care provider.

As an alternative to setting the threshold manually, a preferred embodiment provides that the fall detection system 2 itself is used to measure the time it takes the user 4 to perform certain representative movements or activities, such as an STS transfer, or getting out of bed, during use of the fall detection system 2. For example, the fall detection system 2 can evaluate the signals from the accelerometer 8 and other sensors 16 (if present) to detect when the representative movements or activities are taking place, measure their duration and determine the threshold.

These movements are carried out regularly during the course of a normal day and the time taken to perform these movements can be used to estimate the time (and thus the inactivity period threshold) it would take the user 4 to stand up after a fall. In particular, the fall detection system 2 can determine whether a fall is severe if the user 4 is unable to stand up again within a multiple of this time period. If the user 4 did not stand up, the fall can be considered to be severe.

In further preferred embodiments, if the user 4 does stand up after a fall, the severity of the fall can be graded by evaluating the ratio of the estimated time needed to stand up again (i.e. the inactivity period threshold) and the measured time taken to stand up.

This ratio, or the measured time taken to stand up, can also be used to refine the inactivity period threshold, as described further below.

Figure 4:
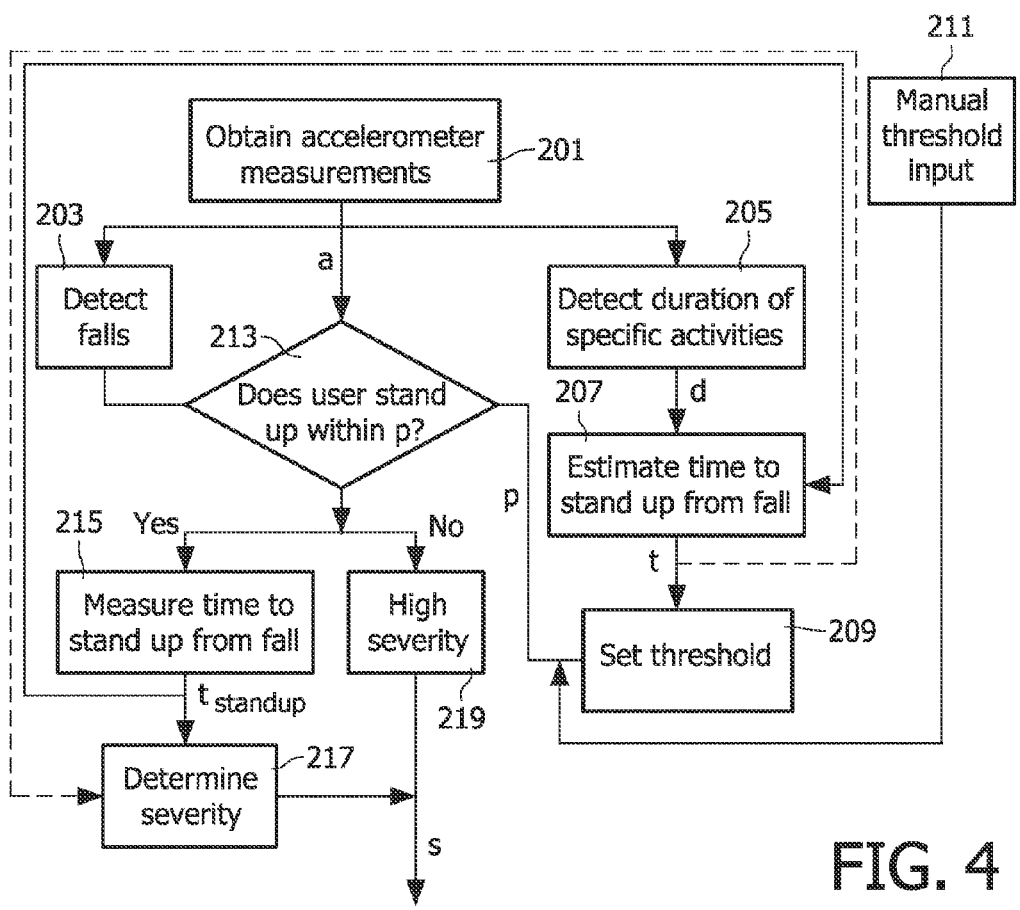
FIG. 4 is a flow chart illustrating another method in accordance with the invention.

FIG. 4 provides a flow chart illustrating the operation of the fall detection system in the preferred embodiment of the invention, in which the threshold, p, is determined from data gathered by the fall detector during its normal operation.

The process starts by monitoring the measurements, a, from the accelerometer 8, and measurements from any other sensors 16 in the fall detection system 2 (step 201).

These measurements are analysed to detect falls (step 203) or to detect the duration of specific activities (step 205), such as an STS transfer, getting up from a bed, etc. Each of these activities has a specific characteristic profile that can be detected from the accelerometer 8 and sensor measurements.

Once an activity has been detected, the duration, d, is used to estimate the time for the user 4 to stand up from a fall (step 207). As described above, the time to stand up from a fall can be determined as a multiple of the duration d, with the value of the multiple depending on the specific activity detected. For example, the time t could be set to d+3 seconds. Alternatively, t could be set to, for example, 2d−1 seconds. Non-linear dependencies, in particular given by a look-up table or by clipping the maximum and minimum values, are also possible.

An alternative option is to maintain a list of the last n detected activity durations. When a new activity duration d is determined, the list can be updated, and the time can be set to, for example, the average or maximum duration of the activities in the list plus 3 seconds.

A further alternative is to use the addition of (for example) two times the standard deviation in the range of durations. This will yield a probability of roughly 2.5% in misclassifying a fall as being severe.

If there are multiple activity types that can be detected, the average or maximum can be taken for each activity separately, and the time t can be set based on the results for each activity type. For example, suppose there are two activities each with respective durations $d_1$ and $d_2$. The time t can then be set to, for example, the maximum of $d_1+3$ and $d_2+1$. The measured duration of each activity is scaled (normalized) to the duration for standing-up from ground level.

Once time t is determined, the threshold, p, is determined (step 209), which indicates how long the user 4 has to stay lying down after a fall, before the fall is classified as severe. It is possible to set p equal to t, but it is preferable to provide the user 4 with additional time to stand up (as they have just fallen), so p can be set equal to, say, t+2 seconds.

To ensure that the fall detection system 2 is able to give a severity classification from first activation (i.e. before the user 4 has performed one of the monitored activities), p can have a default value, possibly determined from one of the manual embodiment tests described above, such as a TUG test, that is used until activities have been detected (step 211).

The threshold p is used by a block 213 to evaluate whether the user 4 stands up within the period p after a fall (as detected in step 203). The measurements from the accelerometer 8 and other sensors 16 (if any) are provided to block 213 in order to determine when the user 4 stands up (this can be indicated by an upwards acceleration (compensated for gravity), a change in orientation, an upwards displacement, etc). Thus, the measurements are monitored to determine the period of time that the user 4 remains on the ground after the fall.

If the user 4 stands up before the time elapsed since the fall reaches the threshold p, the time $t_{standup}$ it took the user 4 to stand up is determined (step 215) and is used to assess the severity s (step 217). In some embodiments, the severity s is simply classified as not severe, as the user has stood up within the time allowed by the threshold.

In alternative embodiments, the severity s can be graded from not severe when the user 4 gets up relatively quickly, up to, say, moderately severe when the user 4 gets up relatively slowly (i.e. the user 4 has used most of the time allowed by threshold to stand up).

The grading can be determined by evaluating the ratio of $t_{standup}/p$ or the ratio $t_{standup}/t$. For example, if the ratio lies between 0.5 and 1, the severity is set to medium, and if the ratio lies between 0 and 0.5, the severity is set to low.

Of course, it will be appreciated that instead of determining a ratio, it is possible to set one or more further thresholds between 0 and p that define when the fall is less severe, moderately severe, etc.

If the user 4 does not stand up within the time allowed by threshold p after the fall, the fall severity s is set to high (step 219).

Based on the determined fall severity s, different services can be started. For example, for a high severity fall, an alarm is raised at a call or service center and possibly emergency services can be summoned. For a fall with lower severity, the fall information can be recorded and/or sent to family members for information or it can be used by physicians to obtain better insight in the fall history of the user 4 and possibly to improve medical treatment. Of course, these steps can also be taken for a high severity fall. A frequent re-occurrence of low-severity falls can be another trigger to alert a care provider that the user 4 might need assistance.

In some embodiments, the time $t_{standup}$ determined in step 215 can also be provided to step 207 to refine and/or update the values of t and p.

In some embodiments, the estimated time to stand up from a fall, t, is also used in determining the severity of the fall (step 217).

In further embodiments of the invention, it is possible to improve the severity estimation by making use of other parameters or characteristics of the signals from the accelerometer 8 and other sensors 16. For example, the magnitude of the impact (i.e. the magnitude of the main acceleration peak, or the sum of the absolute values of three to five of the largest peaks within the impact duration) can be taken into account. Clearly, a large impact indicates a more severe fall. The severity indices, like those derived from impact and inactivity duration, can be combined to determine the overall severity and the necessary alarm action.

Although the invention is described as being for use in a system that is worn by a user 4, it will be appreciated that the invention can be implemented in the form of a surveillance system operated by a care provider, such as in elderly care and nursing homes, or in independent-living facilities.

There is therefore provided a fall detection system and a method of operating a fall detection system that allows the severity of a fall to be determined.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fall detection system, comprising:
   one or more sensors for monitoring movement of a user and for generating corresponding signals;
   a processor configured for:
   determining a threshold from one or more measurements of a physical condition of the user by at least;
   estimating the time it would take the user to stand up after a fall based on the signals; and
   setting the threshold based on the estimated time;
   analyzing the signals to identify a fall by the user;
   analyzing the signals to identify a period of inactivity of the user following the fall; and
   comparing length of inactivity of the user with the threshold to determine severity of the fall.

2. The fall detection system as claimed in claim 1, wherein the processor is adapted to determine that the fall is severe in the event that the length of the period of inactivity of the user exceeds the threshold.

3. The fall detection system as claimed in claim 2, wherein the processor is adapted to trigger an alarm and/or summon help to the user if the fall is severe.

4. The fall detection system as claimed in claim 1, wherein the processor is adapted to analyze the signals to identify the end of the period of inactivity when the user gets up.

5. The fall detection system as claimed in claim 4, wherein the processor is adapted to determine that the fall is not severe in the event that the length of the period of inactivity of the user is less than the threshold.

6. The fall detection system as claimed in claim 4, wherein the processor is adapted to grade the severity of the fall in the event that the length of the period of inactivity of the user is less than the threshold using a ratio of the length of the period of inactivity to the threshold.

7. The fall detection system as claimed in claim 6, wherein the processor is adapted to trigger an alarm and/or summon help to the user in response to the determined severity grade.

8. The fall detection system as claimed in claim 1, wherein the one or more sensors comprises an accelerometer for measuring the acceleration of the fall detection system.

9. The fall detection system as clamed in claim 8, wherein the processor is adapted to identify a fall by identifying an impact that is characteristic of a fall.

10. The fall detection system as claimed in claim 9, wherein the processor is adapted to identify an impact by identifying one or more peaks in the measurements of the acceleration.

11. The fall detection system as claimed in claim 10, wherein the processor is further adapted to determine the severity of the fall by determining the magnitude of the acceleration in the impact.

12. The fall detection system as claimed in claim 1, wherein the one or more measurements of the physical condition of the user comprise measurements of a predetermined movement or series of movements by the user.

13. The fall detection system as claimed in claim 12, wherein the predetermined movement or series of movements comprises one or more of a sit-to-stand transfer, timed up and go movement, getting up from a bed and getting up from the ground.

14. The fall detection system as claimed in claim 12, wherein the one or more measurements comprise measurements of the time taken for the user to complete the predetermined movement or series of movements.

15. The fall detection system as claimed in claim 12, wherein the processor is adapted to determine the one or more measurements of the physical condition of the user while the fall detection system is in use by the user.

16. A method of operating a fall detection system, the method comprising:
   determining a temporal threshold from one or more measurements of user physical condition, the determining including:
   monitoring sensor measurements for specific user activities;

estimating the time it would take the user to stand up after a fall based on the monitored sensor measurements; and setting the threshold based on the estimated time;

detecting a fall by the user; and monitoring length of inactivity of the user following the detected fall relative to the threshold to determine severity of the detected fall.

17. A computer program product for use in a fall detection system, the computer program product comprising a non-transitory computer readable medium carrying computer program code that, when executed on a processor or computer, controls the processor or computer to:

determine a temporal threshold from one or more measurements of user physical condition, the threshold indicating a length of inactivity of the user following a fall and determined by:

monitoring sensor measurements for specific user activities;

estimating the time it would take the user to stand up after a fall based an the monitored sensor measurements; and setting the threshold based on the estimated time;

detect a fall by the user;

monitor length of inactivity of the user following the detected fall relative to the first threshold to determine severity of the detected fall; and grade the severity of the detected fall in response to the length of inactivity of the user being less than the threshold, wherein the grade is based on a ratio of the length of inactivity and the threshold.

18. The fall detection system as claimed in claim 1, wherein the processor is further configured to:

monitor the signals for specific user activities.

19. The fall detection system as claimed in claim 18, wherein the processor is further configured to:

measure the time it takes the user to stand up from a chair, walk three meters, turn around, walk back and sit down; and estimate the time it would take the user to stand up after a fall based on the measured time.

20. The fall detection system as claimed in claim 1, wherein the threshold is re-evaluated at regular intervals while monitoring movement of the user.

\* \* \* \* \*